United States Patent [19]

Hood et al.

[11] Patent Number: 4,712,722
[45] Date of Patent: Dec. 15, 1987

[54] CONCURRENT ULTRASONIC WELD EVALUATION SYSTEM

[75] Inventors: Donald W. Hood; John A. Johnson; Herschel B. Smartt, all of Idaho Falls, Id.

[73] Assignee: EG&G, Inc., Wellesley, Mass.

[21] Appl. No.: 772,527

[22] Filed: Sep. 4, 1985

[51] Int. Cl.$^4$ ............ B23K 5/22; B23K 9/32; B23K 37/00
[52] U.S. Cl. ............ 228/104; 228/9; 228/56.5
[58] Field of Search ............ 228/104, 9, 565; 73/620, 628

[56] References Cited

U.S. PATENT DOCUMENTS

| | | | |
|---|---|---|---|
| 3,156,110 | 11/1964 | Clynes | 73/628 |
| 3,552,191 | 1/1971 | Heseding | 73/625 |
| 3,958,451 | 5/1976 | Richardson | 73/625 |
| 4,144,766 | 3/1979 | Wehrmeister | 228/104 |
| 4,305,297 | 12/1981 | Ries et al. | 73/628 |
| 4,413,520 | 11/1983 | Murakami et al. | 73/628 |
| 4,419,562 | 12/1983 | Jon et al. | 228/104 |
| 4,487,070 | 12/1984 | Gerling et al. | 73/628 |
| 4,524,622 | 6/1985 | Suzuki et al. | 73/628 |

FOREIGN PATENT DOCUMENTS 794488 1/1981 U.S.S.R. ............ 228/104

OTHER PUBLICATIONS

"Weld Energy Reduction By Using Concurrent Nondestructive Evaulation: Independent Systems Plate Tests", Johnson and Smartt, EG&G Idaho, Inc., Internal Technical Report, Materials Science Division, Mar., 1984.

*Primary Examiner*—Nicholas P. Godici
*Assistant Examiner*—Samuel M. Heinrich
*Attorney, Agent, or Firm*—Hugh W. Glenn; Robert J. Fisher; Robert P. Cogan

[57] ABSTRACT

A system for concurrent, non-destructive evaluation of partially completed welds for use in conjunction with an automated welder. The system utilizes real time, automated ultrasonic inspection of a welding operation as the welds are being made by providing a transducer which follows a short distance behind the welding head. Reflected ultrasonic signals are analyzed utilizing computer based digital pattern recognition techniques to discriminate between good and flawed welds on a pass by pass basis. The system also distinguishes between types of weld flaws.

19 Claims, 5 Drawing Figures

CONCURRENT ULTRASONIC WELD EVALUATION SYSTEM

CONTRACTUAL ORIGIN OF THE INVENTION

The United States Government has rights in this invention pursuant to Contract Number DE-AC07-76ID01570 between the United States Department of Energy and EG&G Idaho, Inc.

BACKGROUND OF THE INVENTION

This invention relates generally to non-destructive evaluation of welds and more particularly to a method and apparatus for non-destructive concurrent evaluation of partially completed welds to permit detection and identification of welding flaws during the welding process.

Modern procedures for industrial arc welding of critical parts for such products as aircraft, ships and nuclear power plants normally require non-destructive evaluation of the integrity of the welds and repair of any defects that would impair the use of these parts. In such applications, most welds are produced by making multiple passes in a prepared joint configuration, frequently using mechanized welding equipment and then the completed weld is evaluated using known non-destructive evaluation techniques. The most common prior art techniques utilize radiography employing x-ray techniques and ultrasonics using ultrasonic sound to inspect the interior of the weld. If a weld defect is detected with dimensions in excess of those allowed by applicable codes, as a result of the non-destructive evaluation of the completed weld, the defect must be removed and the weld repaired.

The repair of a defect is begun by exploratory grinding. If the defect is in a deep weld (i.e. covered by subsequent multiple passes) a lot of otherwise good weld deposits are ground out to remove the defect. The part must then be rewelded and the weld reinspected. This process entails high materials energy and labor costs. Many of these costs can be eliminated or dramatically reduced and substantial labor productivity gains could be achieved by a concurrent evaluation system which could detect the flaws soon after they are produced and before they are covered with succeeding weld passes.

In such a concurrent evaluation system it would be highly desirable to be able to detect and distinguish welding flaws; (1) porosity, and (2) lack of fusion. Porosity is the presence of bubbles or pores in the weld metal. Usually some porosity is acceptable depending upon the distance between the bubbles and the overall length of the defect. Lack of fusion occurs when the weld metal does not wet and fuse with the parent metal. Most acceptance codes do not allow any lack of fusion and thus all lack of fusion flaws must be repaired. Hence, it is highly desirable to be able to distinguish types of flaws with any concurrent evaluation system in order to assure that the unnecessary repairs are not made and necessary repairs are made.

It is accordingly an object of this invention to provide a novel concurrent weld evaluation system for near real-time evaluation of partially completed welds.

It is another object of the invention to provide a novel concurrent weld evaluation system utilizing near real-time ultrasonic inspection in conjunction with computerized pattern recognition analysis of ultrasonic echoes.

It is yet another object of the invention to provide a novel concurrent weld evaluation system utilizing pattern recognition analysis of ultrasonic echoes to detect welding flaws in partially completed welds and distinguish types of welding flaws.

It is yet another object of the invention to provide a novel concurrent weld evaluation system utilizing an ultrasonic search head following a predetermined distance behind a automated welder utilizing computer pattern recognition analysis of reflected ultrasonic energy to identify the location of welding flaws and distinguish between types of flaws.

Briefly, according to one embodiment of the invention, apparatus is provided for concurrent non-destructive evaluation of partially completed welds for use in conjunction with an automated welder. The apparatus includes an ultrasonic generator mounted in fixed proximate relationship to the welder for generating pulses of ultrasonic signals and for coupling the ultrasonic signals in real-time to the region of the partially completed weld. In addition, an ultrasonic detector is provided for detecting ultrasonic signals reflected from the region of the partially completed weld and analysis means is provided for processing the detected ultrasonic signals and identifying weld flaws in a response thereto.

BRIEF DESCRIPTION OF THE DRAWINGS

The invention, together with further objects and advantages thereof, may be understood by reference to the following description taken in conjunction with the accompanying drawings.

DETAILED DESCRIPTION OF THE PREFERRED EMBODIMENT

Figure 1:
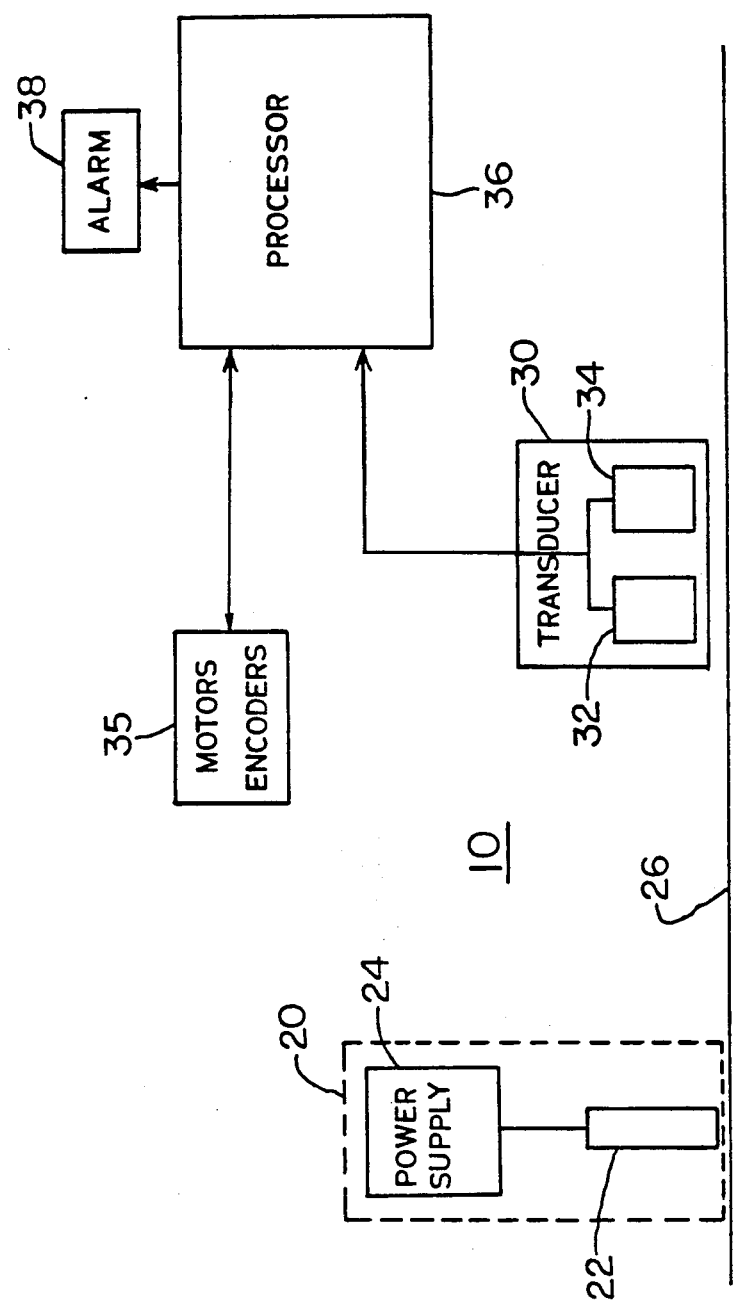
FIG. 1 is a generalized block diagram of a specific embodiment of a concurrent ultrasonic welding evaluation system according to the invention.

FIG. 1 is a generalized block diagram illustrating a specific embodiment of a concurrent ultrasonic weld evaluation system 10 according to the invention. The system 10 includes a mechanized or automated welder 20 (e.g. a Linde Side Beam Weld Machine, Model HWM-4A, using a Linde Control Console, Model HWC-3 and a Miller D.C. Arc Welding Power Supply, Model 300) having moving welding head 22 which may be an arc welder utilizing a consumable welding electrode with a welding head which is powered and controlled by a conventional power supply and control circuit 24, as shown. During a welding operation the welding head 22 is automatically moved along making multiple passes in a prepared joint surface 26 to be welded. Defects may be created during this process due to numerous variables resulting welding flaws such as porosity or lack of fusion.

As illustrated in FIG. 1, a transducer assembly 30 is mounted so as to remain a predetermined distance (e.g. 13 inches in the illustrated embodiment) behind the welding head 22. In one embodiment, a set of motors and position encoders 35, controlled by the processor 36 as shown, maintain the proper position of the transducer assembly 30 and permit adjustment of the position and orientation of the transducer. The transducer assembly 30 comprises a conventional ultrasonic transducer which generates ultrasonic sound signals which are coupled to the weld region.

Figure 2B:
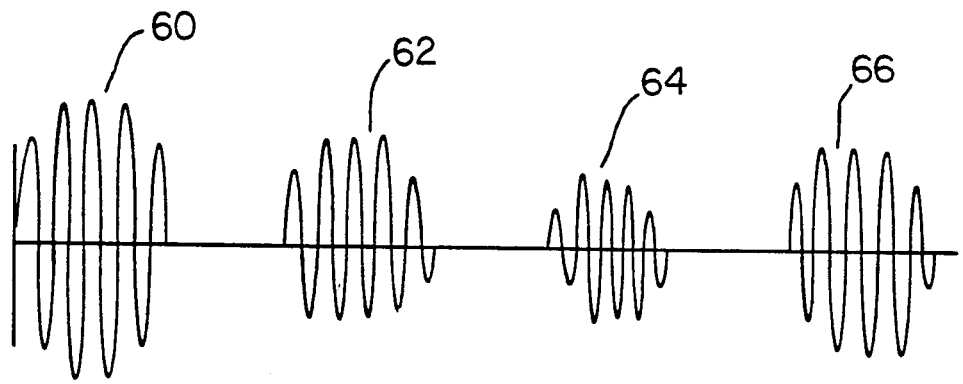
FIG. 2B is an amplitude vs time graph of a typical ultrasonic pulse and associated reflections.
Figure 2A:
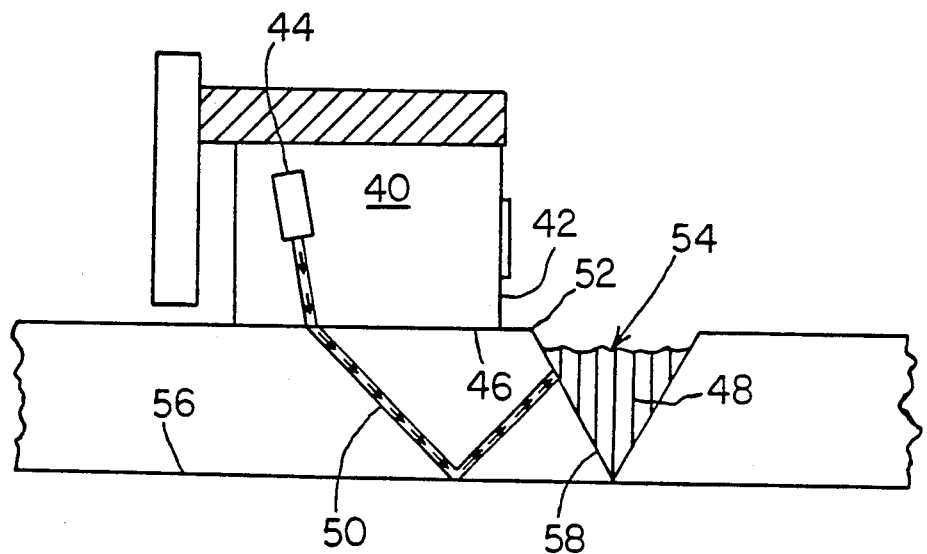
FIG. 2A is a diagramatic illustration of a specific embodiment of an ultrasonic search head and the ultrasonic beam path.

One conventional method of coupling the ultrasonic signals to the weld region is illustrated in FIG. 2A. A transducer assembly 40, comprising a liquid filled tire 42 with a transducer 44 mounted within (e.g. such as those marketed by Ultra-Image International, Inc.) is configured in close proximity to the surface of the welded surface 46 and to the partially completed weld 48 so as to couple ultrasonic sound into the region of the weld. Using a pulse-echo technique, a beam 50 of ultrasonic pulses is generated and transmitted from the tire 42 to the surface 46 of the material being welded where it is partially reflected and partially transmitted into the body of the material. All discontinuities in sound speed and/or density in the region of the weld will result in reflections, thus those due to flaws and those due to benign, geometric surfaces will produce reflections. Since the geometric reflectors are known, they are separated from any flaw signals by signal processing techniques. The reflected ultrasonic pulses can be detected by a second receiving transducer 34 or as illustrated in FIG. 2A, are detected by the single transducer 44. The reflected signals may have a form such as illustrated in FIG. 2B where the original pulse 60 is followed by reflections 62, 64, 66 from various surfaces and discontinuities.

The partially completed weld 48 of FIG. 2A has several geometric reflectors which must be distinguished from possible flaw reflectors. In the illustrated embodiment, the ultrasonic pulses come in at an angle to the surface 46 of the material. The reflection from a surface such as the bottom surface 56 is normally mirror-like or specular and thus little energy is reflected directly back to he transducer 44. When the reflected beam 50 of pulse intersects the weld root 58, significant reflection back to the transducer are produced due to irregularities in the surface. The top corner of the weld preparation 52 and the top of weld fill 54 also produce reflections that must be separated from flaw reflections.

Referring again to FIG. 1, a first transducer 32 generates ultrasonic signals which are detected by a second transducer 34. The second transducer 34 may be eliminated and the first transducer 32 may be used as a detector as well as a transmitter, as illustrated in FIG. 2A. The detected signals are coupled, as shown, to a processor 36 which processes the signal using pattern recognition techniques to identify flaws and eliminate geometric reflections.

In an alternative embodiment, the second transducer 34 is located on the opposite side of the weld as the first transducer 32, to permit ultrasonic evaluation from both sides of the weld thereby enhancing ability to detect lack of fusion flaws. One approach utilizes two widely separate ultrasonic frequencies to permit simultaneous evaluation from each side of the weld while another approach utilizes pulses at different instants in time to evaluate both sides of the weld. Another embodiment provides for moving a single transducer from one side of the weld to the other to permit evaluation from both sides of the weld. In addition, the evaluation transducer is configured at different positions for each welding pass to compensate for the more complete fill of the weld after each pass. In the illustrated embodiment, the transducer is turned approximately four degrees from perpendicular to edge of the weld preparation 52 (i.e. referring to FIG. 2A, four degrees out of the plane of the page) to reduce geometric reflection from the corners of the weld and from the weld preparation by taking advantage of the largely specular nature of these reflectors. The processor 36 of FIG. 1 thus is aided in separating flaws from benign geometric reflections by the fact that reflections from flaws are more diffuse and return larger reflection signals to the transducer.

In the illustrated embodiment, a set of reflection data based upon an ultrasonic pulse is taken approximately every tenth of an inch along the weld on each side. This data is stored in memory within the processor 36 and is processed using digital pattern recognition techniques to automatically separate out the benign geometric reflection and identify whether the flaw is a porosity flaw or a lack of fusion flaw. If a flaw is detected, the processor determines whether these flaws exceed predetermined limits permitted (e.g. length of flaw) by applicable codes based on specifications stored in memory. In the illustrated embodiment, if a flaw is detected in a single set of data with no flaw detected in data taken on either side, the flaw detection is ignored. If the flaw size exceeds the predetermined limits, an alarm or other communication (e.g. flashing light, printout, etc.) to an operator is produced by a communications device 38 which is activated by the processor 36. In one embodiment, the communication device 38 marks the location of each detected flaw as the system moves along the weld also indicating the type of flaw. The processor 36 thus identifies in real-time the existence of flaws and the type of flaw as well as the location of any identified flaws thereby permitting repair of the flaw before the next pass is begun. In still another embodiment the processor 36 automatically stops the welding process and/or activates an alarm if the total number of flaws detected exceeds a predetermined number, since this is an indication that the system is not working properly.

Figure 3:
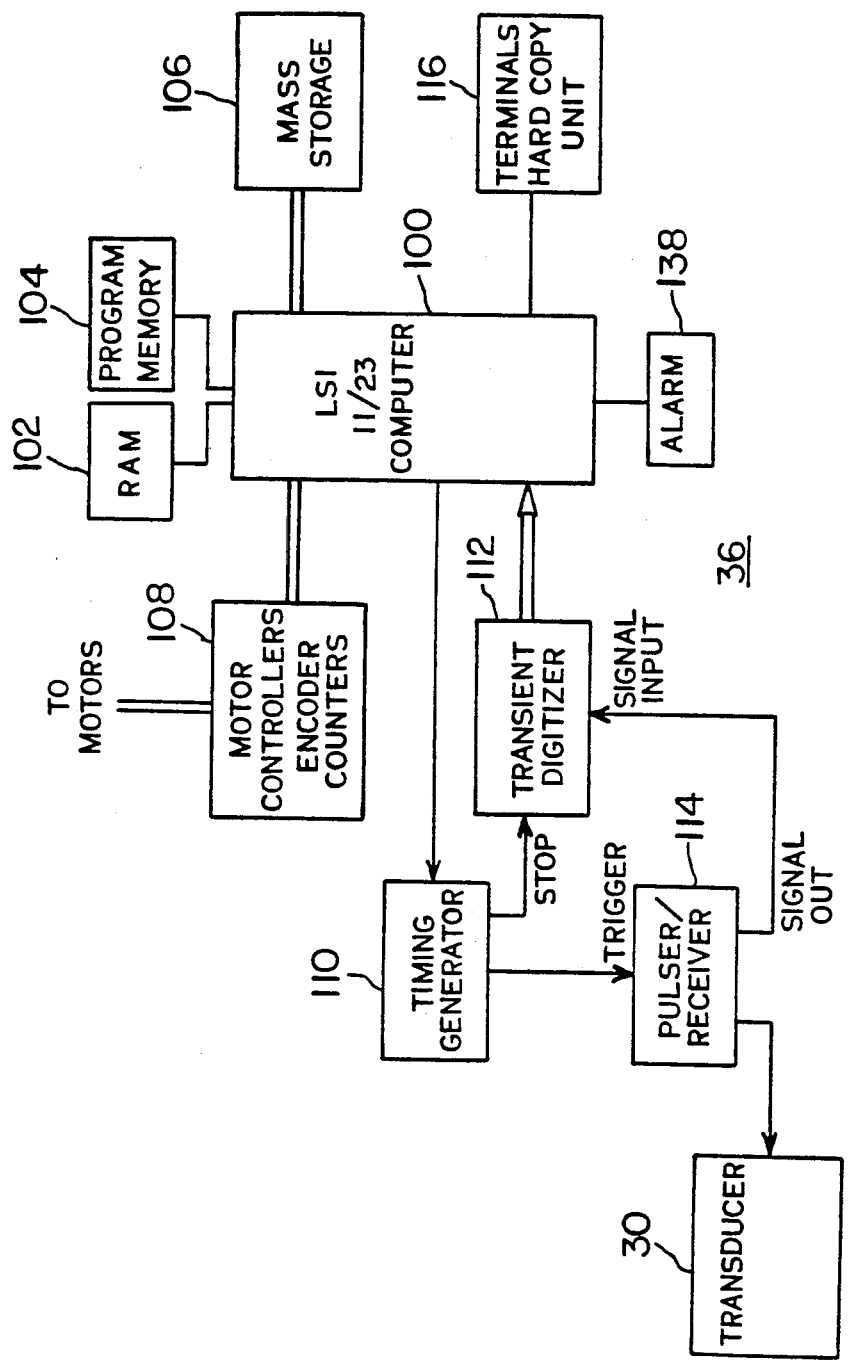
FIG. 3 is a detailed block diagram of a specific embodiment of the concurrent ultrasonic evaluation system processor logic and associated circuitry according to the invention.

FIG. 3 is a detailed block diagram illustrating a specific embodiment of the processor logic 36 shown in FIG. 1. A central computer 100 provides the primary processing capability, and in the illustrated embodiment is a programmed digital computer such as a Digital Equipment Corp. LSI 11/23. Program memory 104 and random access memory 102 are coupled, as shown, for storage of program code and other data. A mass storage device 106, such as a conventional Winchester Magnetic Disk Storage system is coupled to the computer 100 to provide large scale, non-volatile storage of data. Also coupled to the computer 100 is an alarm output device 138 for indicating flaws or system malfunction, and a terminal output 116 to permit print out of data analysis results such as identified flaws and their locations.

The processor 36 communicates with motor controllers and counters 108, a timing generator 110, and a transient digitizer 112, configured as shown. On command from the computer 100, the motors are moved to the required position and the encoder counters are read out thereby recording the actual position of the transducer assembly 30. Then the computer 100 signals the timing generator 110 to start the acquisition process. The timing generator sends a trigger signal to a pulser/receiver 114 which then sends electrical pulses to the transducer causing transducer to generate ultrasonic sound signals (at a frequency of 2.5 MHZ in the illustrated embodiment). After a specified delay (e.g. approximately 70 to 80 microseconds, long enough to exclude undesired early reflections such as those from top and bottom surfaces), the timing generator sends a stop signal to the transient digitizer 112 and the received reflection data is read out from the pulser/receiver, sampled and digitized by the digitizer 112, and stored by the computer 100 on the mass storage device 106. This stored reflection data is then analysed using pattern recognition techniques to identify welding flaws.

In general, the analysis performed by the computer 100 to distinguish flaws from benign reflections is a specialized pattern recognition system. A set of features (i.e. numbers) are derived from each set of reflection data. These features are then compared with a reference set of features stored in the processor memory 104. These reference features are obtained from reflection data on known flawed welds and known unflawed welds. A decision is made as to whether the features of the incoming reflection data match those of flawed or unflawed areas. This decision is based on the Euclidean distance between the derived features of the set of reflection data and the centroid of each reference set. The set of reflection data is then classified as belonging to the reference set classification to which it is closest.

One set of derivable features which may be used for the pattern recognition analysis are autoregressive coefficients, also known as linear-predictive coefficients. This approach is essentially an attempt to predict the next value in a sequence of values by using several previous values according to the formula:

$$\text{Estimate } [y(n)] = \sum_{i=1}^{k} a_i y(n - i)$$

where the y value are amplitudes for reflected signals taken at equal time intervals and the a's are the autoregressive coefficients. The coefficients are determined by minimizing the error between the calculated value and the actual value. These autoregressive coefficients are numbers which represent the pattern of the particular set of reflection data thus are suitable for use as features in the pattern recognition system.

Another type of derivable features which may be used for the pattern recognition analysis are the autocorrelation coefficients of the set of reflection data being analyzed. These coefficients depend largely upon the shape of the reflected waveform and are calculated according to the following formulae:

$$P_R = \frac{c_k}{c_o} \text{ where}$$

$$C_k = \frac{1}{N} \sum_{i=1}^{N=k} [y(k) - \bar{y}][y(k + i) - \bar{y}], k = 0, 1, 2, \ldots K$$

where N is the number of data points in the set of reflection data, y(i) is a data point, and $\bar{y}$ is the average of all the data and K is the number of autoregressive coefficients. Thus, essentially, each autocorrelation coefficient represents the integral of the product of the data times itself shifted in time.

Still another approach to deriving features from the reflection data for pattern recognition analysis is based upon cues similar to those used by a human in analysing plots of reflection waveforms. In general, it has been observed by the inventors that the lack of fusion reflection signal is of greater amplitude than that of porosity and tends to be a replica of the original pulse waveform from the transducer. A porosity flaw reflection signal consists of several reflections from the bubbles in the porosity, which overlap resulting in many cycles in the waveform. The reflected signal from a good weld will have no amplitude above a threshold. Based upon these characteristics, a derivable set of features together with a set of input parameters, three of which are related to the gain of the system, are highly effective when used for pattern recognition analysis of reflection data to identify welding flaws.

The input parameters include a first and a second threshold, a gain factor and consecutive peak interval. The first threshold is used to eliminate small noise signals from the analysis by ignoring any small amplitudes if they are below this value. The second threshold is used to discriminate between the high amplitude lack of fusion signals and the lower amplitude porosity and geometric reflector signals. The gain factor is used to weight the three features which are amplitudes in order to permit compensation for different gain settings. If the system is calibrated before use to a consistent calibration standard, then input parameters can be set to constant values.

The last input parameter, the range for consecutive cycles, is used to define the number of cycles in a reflection in order to discriminate between porosity with many cycles, and lack of fusion with few cycles. The reflection data is stored as a series of numbers, each representing the amplitude of the reflection waveform at a particular instant in time. The data is acquired by sampling the reflected signal every 50 nanoseconds (ns) in the illustrated embodiment. The expected time between cycles is determined by the frequency used by the transducer and in the illustrated embodiment is about 400 ns. Thus, each cycle is expected to be within about eight data points (400 ns/50 ns), which means the range for consecutive cycles should be approximately eight. To determine how many cycles are in a group, a positive peak is located and the data is checked to determine if there is another positive peak above the first threshold within the next eight data samples. This process is repeated until a peak is not found thereby determining the number of cycles in the group. The range of consecutive peaks is chosen to be ten instead of eight in the illustrated embodiment to allow for slight variations in the signal frequency.

The amplitude features are the three highest amplitudes above the first threshold multiplied by the gain factor so as to weight the amplitudes to a consistent scale. These features are important for distinguishing lack of fusion reflections from other reflectors since the lack of fusion flaws produce the highest amplitudes. A second set of features used is the number of consecutive peaks or cycles of the two largest groups of peaks in the set of reflection data within the range defined by the consecutive peaks range input parameter. These features are important for distinguishing between lack of fusion and porosity, for example, for lack of fusion and geometric reflector the number of peaks should be approximately six to eight, while for porosity the number of peaks should be from approximately twelve to sixteen. Two additional features are obtained by dividing the reflection data into segments (bins) and calculating the number of bins with values above the first threshold and above the second threshold.

In identifying flaws in these features, lack of fusion reflection will produce the highest amplitudes, with porosity signals next highest and good welds significantly lower than either. Thus good welds are distinguished from flaws by the amplitude of the three amplitude features and the amplitude difference between flaw types is an aid in distinguishing between flaw types. The length in cycles (peaks) of the two longest groups is used to distinguish between lack of fusion and porosity, with porosity typically having twice the number of peaks. The number of bins above the two thresholds is also used to distinguish between flaw types, with the number of bins twice as high for lack of fusion as for porosity.

Some typical values were developed using a system with an ultrasonic signal frequency of 2.5 Mhz, and the above input parameters while welding ½ inch thick type A-36 carbon steel plates. The input parameters used were a first threshold of 0.17 v, a second threshold of 0.40 v, a gain factor of 1 to 1.2, and a consecutive cycle range of 10. The mean amplitude values for lack of fusion reflections exceeded 0.26 volts, those for porosity were between 0.17 v and 0.23 v, while those for good welds were below 0.06 v. Using these values good results for identifying good and flawed welds are obtained, with some indication of flaw type. The mean number of bins above the first threshold were 2 for good welds, above 7 for porosity flaws, and above 11 for lack of fusion. Thus these features provide additional pattern analysis information to aid in identifying flaws. The cycle length of the two largest groups is the most useful feature to distinguish between lack of fusion and porosity with lack of fusion producing cycle length of 8 or less and porosity of more than 8.

It should be noted that this pattern recognition method permits tuning of the system to specific requirements. Thus, user input of thresholds allows adjustment to favor a few false calls to ensure finding flaws, or vice versa. For example, higher values of the input threshold would reduce the number of false calls while resulting in missing some small porosity flaws. Conversely, lower values of the input thresholds would reduce the number of flaws missed, but at the cost of a higher false call rate.

Figure 4:
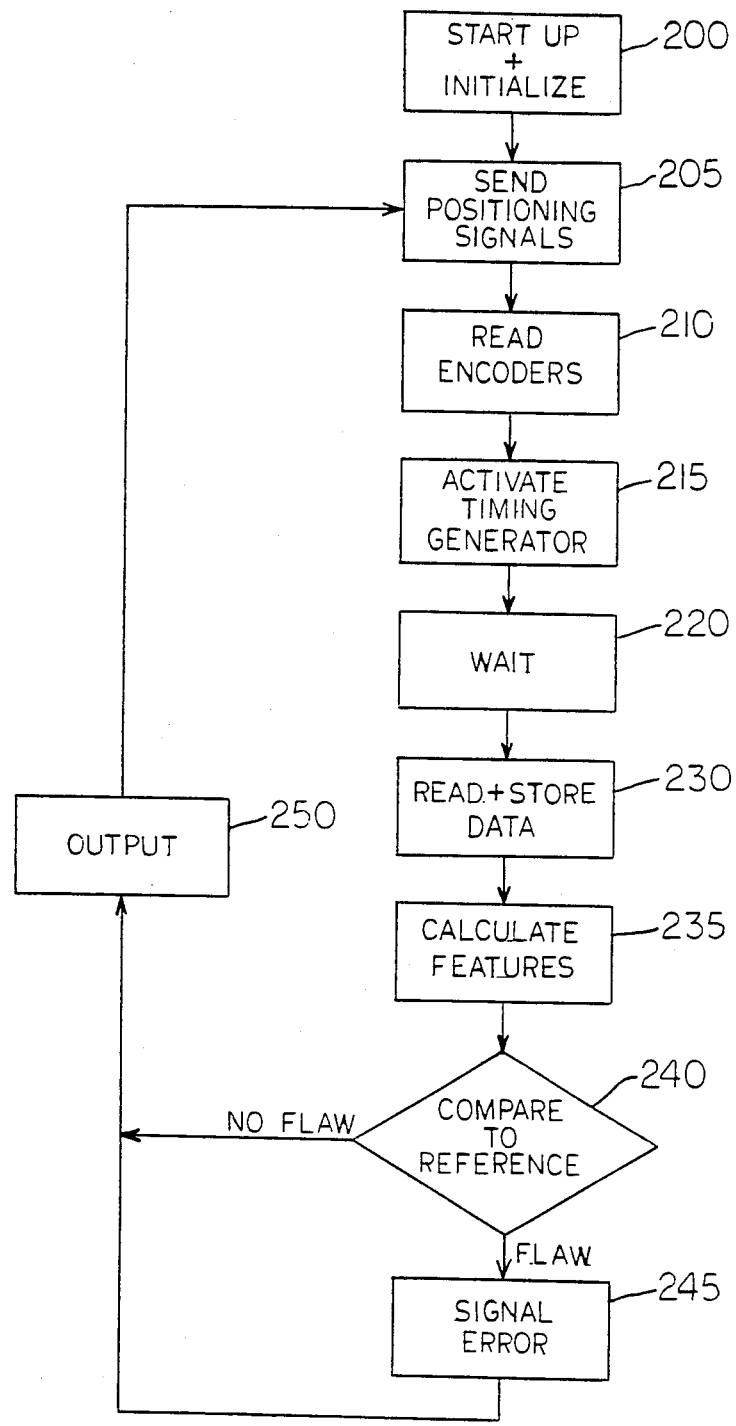
FIG. 4 is a flow diagram of the software flow for the programmed computer shown in FIG. 3.

Referring now to FIG. 4, there is shown a flow diagram of the software flow for the programmed computer 100. The program begins as shown at 200, with start-up and initialization of values, such as the input parameters which can be predetermined or entered by an operator upon start-up. The computer, then generates positioning signals which are coupled to the motor controller 108, as shown at block 205 and reads the position encoder to determine the actual motor position as indicated at block 210. The computer then, at block 215, generates an activation signal to activate the timing generator 110 which causes the timing generator to send a trigger signal to the pulse generator 114 which pulses the transducer 30. The computer then waits a predetermined delay at 220 (e.g. approximately 75 μs in the illustrated embodiment) and at block 230, after the stop signal has been generated by the timing generator, reflection data is read from the transient digitizer 112 and stored in the mass storage device 106 as indicated at block 235. Each set of data comprises approximately 400 samples in the illustrated embodiment. This data is subsequently processed to calculate the features as described hereinbefore. The results are then compared to the reference feature data and at block 240 a classification decision is made based upon the Euclidean distance between the centroid of each reference set and the reflection data features. If a flaw is detected an error signal is generated to activate the flaw indicator as illustrated at block 245. The flaw indicator may be an audio or visual alarm or may be a marking device to mark the location of the flaw. If no flaw is detected, and after generation of the error signal, the program control returns to block 205. In addition, at block 250, and also at wait block 220, results may be output to a print spooler to provide a hard copy of results, if desired.

Specific embodiments of the concurrent ultrasonic weld evaluation system have been described for purposes of illustrating the manner in which the invention may be made and used. It should be understood that implementation of other variations and modifications of the invention in its various aspects will be apparent to those skilled in the art, and that the invention is not limited by the specific embodiments described. It is therefore contemplated to cover by the present invention any and all modification, variations, and equivalents that fall within the true spirit and scope of the basic underlying principles described and claimed herein.

What is claimed:

1. Apparatus for concurrent non-destructive evaluation of partially completed welds for use in conjunction with an automated welder, comprising:
   (a) generating means, mounted to maintain in predetermined fixed proximate spatial relationship to the automated welder, for generating ultrasonic signals and for coupling the ultrasonic signals in real-time to the region of the partially completed weld;
   (b) detection means for detecting ultrasonic signals reflected within a reflection period of predetermined resolution from the region of the partially completed weld; and,
   (c) analysis means for processing in real-time the ultrasonic signals within the reflection period detected by the detection means to identify welding flaws in response thereto.

2. The apparatus of claim 1 wherein the analysis means comprises a digital computer programmed to perform pattern recognition.

3. The apparatus of claim 1 wherein the analysis means comprises means for distinguishing between a plurality of preselected types of welding flaws.

4. The apparatus of claim 1 wherein the generating means couples ultrasonic signals to and the detection means receives signals reflected from the region of the weld respectively at an angle of 4° from perpendicular to the weld edge.

5. The apparatus of claim 1 wherein the generating means generates pulses of ultrasonic sound.

6. The apparatus of claim 1 further comprising communication means to indicate the identification of flaws exceeding predetermined limits.

7. The apparatus of claim 6 wherein the communication means comprises means for marking the location of each flaw exceeding the predetermined limits.

8. The apparatus of claim 6 further comprising means for totalling the number of flaws detected for each pass of the automated welder and means for inhibiting operation of the automated welder in response to the total number of flaws exceeding a predetermined number.

9. The apparatus of claim 1 wherein the generating means generates ultrasonic signal pulses on each lateral side of the partially completed weld and the detection means detects ultrasonic signal pulses reflected from the region of the partially completed weld on each side of the partially completed weld.

10. The apparatus of claim 7 wherein the means for marking comprises means for indicating the types of each flaw marked.

11. The apparatus of claim 9 wherein the ultrasonic pulses generated are of a different frequency on each side of the partially completed weld.

12. The apparatus of claim 1 further comprising location means for determining the position of the generating means and output means for providing a printed output of flaw locations.

13. A method of concurrent, non-destructive evaluation of partially completed welds of an automated welder, comprising the steps of:
  (a) generating ultrasonic signals;
  (b) coupling the ultrasonic signals in real time to the region of the partially completed weld in close proximity to the automated welder;
  (c) detecting ultrasonic signals reflected from the region of the partially completed weld;
  (d) grouping detected ultrasonic signals within preselected time periods; and,
  (e) individually processing detected groups of ultrasonic signals to identify welding flaws.

14. The method of claim 13 further comprising the step of generating a signal indicating welding flaws in response to identification of welding flaws exceeding predetermined specifications.

15. The method of claim 14 further comprising the step of repairing partially completed welds in response to identification of welding flaws exceeding the predetermined specification.

16. The method of claim 13 wherein the step of processing further comprises the step of identifying one of a plurality of types of welding flaws and identifying the location of each welding flaw.

17. The method of claim 13 wherein the step of generating ultrasonic signals comprises generating pulses of ultrasonic signals.

18. The method of claim 13 wherein the step of coupling ultrasonic signals comprises coupling the signals to the region of the weld at a predetermined non-zero angle from perpendicular to the weld edges.

19. A system for automated, multiple pass welding with concurrent non-destructive evaluation of partially completed welds, comprising;
  (a) automated welding means, including a welding head, for welding metal components;
  (b) transducer means, mounted in predetermined spatial relationship to the welding head, for generating ultrasonic pulses and coupling those pulses to the region of the partially completed weld and for detecting reflected ultrasonic pulses;
  (c) location means for generating location data responsive to the location of the transducer means;
  (d) processor means for processing in real-time the detected reflected ultrasonic pulses resolved into groups of pulses reflected from their locations within a time period of preselected resolution and the location data to identify welding flaws represented by respective groups and their location.

* * * * *